United States Patent [19]
Parra

[11] Patent Number: 6,034,485
[45] Date of Patent: Mar. 7, 2000

[54] LOW-VOLTAGE NON-THERMIONIC BALLAST-FREE ENERGY-EFFICIENT LIGHT-PRODUCING GAS DISCHARGE SYSTEM AND METHOD

[76] Inventor: Jorge M. Parra, 5210 Sycamore Dr., New Port Richey, Fla. 34654

[21] Appl. No.: 08/964,824

[22] Filed: Nov. 5, 1997

[51] Int. Cl.[7] ............................................. H05B 37/02
[52] U.S. Cl. ........................... 315/209 R; 315/200 R; 315/242; 315/105
[58] Field of Search .............................. 315/209 R, 105, 315/94, 107, 95, 96, 97, 98, 99, 100, 101, 102, 103, 104, 106, 242, 200 R

[56] References Cited

U.S. PATENT DOCUMENTS

| | | |
|---|---|---|
| Re. 33,057 | 9/1989 | Clegg et al. . |
| 1,963,963 | 6/1934 | Barclay . |
| 2,139,815 | 12/1938 | Fodor . |
| 3,975,660 | 8/1976 | Knobel et al. . |
| 4,005,330 | 1/1977 | Glascock, Jr. et al. . |
| 4,010,400 | 3/1977 | Hollister . |
| 4,189,661 | 2/1980 | Haugsjaa et al. . |
| 4,196,374 | 4/1980 | Witting . |
| 4,266,167 | 5/1981 | Proud et al. . |
| 4,410,930 | 10/1983 | Yachabach . |
| 4,427,923 | 1/1984 | Proud et al. . |
| 4,630,005 | 12/1986 | Clegg et al. . |
| 4,782,268 | 11/1988 | Fähnrich et al. . |
| 4,798,997 | 1/1989 | Egami et al. ........................... 315/115 |
| 4,808,887 | 2/1989 | Fähnrich et al. . |
| 4,857,806 | 8/1989 | Nilssen . |
| 4,920,299 | 4/1990 | Presz et al. ................................. 315/98 |
| 4,949,013 | 8/1990 | Zuchtriegel . |
| 4,959,591 | 9/1990 | Hirschmann . |
| 4,973,885 | 11/1990 | Kerwin . |
| 5,140,224 | 8/1992 | Kakitani et al. ..................... 315/209 R |
| 5,300,860 | 4/1994 | Godyak et al. . |
| 5,325,024 | 6/1994 | Piejak et al. . |
| 5,349,270 | 9/1994 | Roll et al. . |
| 5,359,263 | 10/1994 | Roberts . |
| 5,365,145 | 11/1994 | Fields ........................................ 315/86 |
| 5,381,073 | 1/1995 | Godyak et al. . |
| 5,408,162 | 4/1995 | Williams . |
| 5,461,286 | 10/1995 | Hirschmann ............................ 315/205 |
| 5,512,801 | 4/1996 | Nilssen . |
| 5,521,467 | 5/1996 | Statnic et al. . |
| 5,548,189 | 8/1996 | Williams . |
| 5,578,907 | 11/1996 | Tao et al. . |
| 5,581,161 | 12/1996 | Gong . |
| 5,666,031 | 9/1997 | Jennato et al. .......................... 315/246 |

OTHER PUBLICATIONS

Peter N. Wood and Gerry Limjuco, "Simple Electronic Ballast Using IR2155 MOS Gate Driver", *International Rectifier Publication Application Notes*, No. DT 94–3, pp. 1–11.

Peter N. Wood, "Electronic Ballasts Using the Cost–Saving IR2155 Driver", *International Rectifier Publication Application Notes*, No. AN–995, pp. 1–3.

*Primary Examiner*—Don Wong
*Assistant Examiner*—James Clinger
*Attorney, Agent, or Firm*—Jim Zegeer

[57] ABSTRACT

A system of igniting a gas discharge device having spaced electrodes immersed in a gas, at voltages below the required starter ignition voltage for cold cathodes. A square wave alternating voltage source of between about 75 kHz and 4 MHz is applied directly to the gas discharge device so that the voltage on the spaced electrodes reverses its polarity more rapidly than the pattern of electron and ion density in the gas can shift.

49 Claims, 6 Drawing Sheets

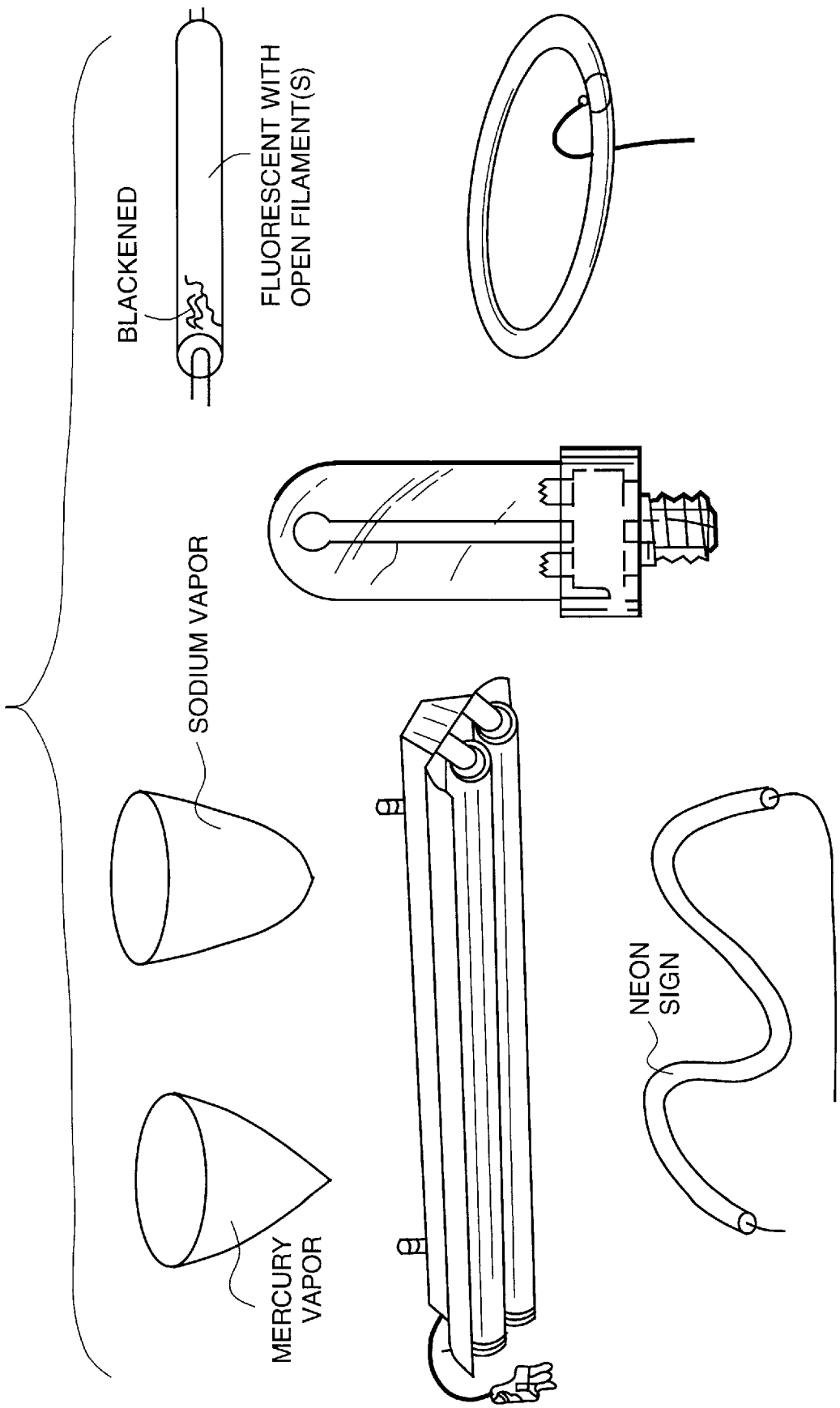

LOW-VOLTAGE NON-THERMIONIC BALLAST-FREE ENERGY-EFFICIENT LIGHT-PRODUCING GAS DISCHARGE SYSTEM AND METHOD

This application is related to U.S. application Ser. No. 08/942,670 filed Oct. 2, 1997 entitled LOW-VOLTAGE NON-THERMIONIC BALLAST-FREE FLUORESCENT LIGHT SYSTEM AND METHOD which in turn was the subject of provisional application Ser. No. 60/053,796 filed Jul. 25, 1997 which are incorporated hereby reference.

Reference is also made to my application Ser. No. 08/915,696 filed Aug. 21, 1997 entitled LOW-VOLTAGE HIGH-EFFICIENCY FLUORESCENT SIGNAGE, PARTICULARLY EXIT SIGN and incorporated herein by reference.

BACKGROUND AND BRIEF DESCRIPTION OF THE INVENTION

The present invention relates to gas discharge light-producing systems and methods and, more particularly, to low-voltage, low-current, non-thermionic (e.g., no heated filament) ballast-free energy-efficient light-producing systems and methods which are more efficient, less expensive, substantially free of RF emissions and which can use conventional industrial, commercial or home gas discharge lamps (fluorescent tubes of various shapes and sizes, high-intensity discharge lamps, sodium vapor lamps, mercury vapor lamps, neon signage tubes).

In most commercial and home-grade fluorescent lighting systems, the heart of the system is the ballast, which is an inductance or transformer device that boosts the incoming voltage to a higher voltage level to start the fluorescent tubes and then, once the fluorescent tubes are lit or ignited (gas ionized or discharged), reduces the voltage to a level for normal continuous lighting. Moreover, these prior systems often use transformer filament windings to heat the filaments to therefore provide thermionic emission for assisting in the ignition phase. Heated filaments vaporize and form black deposits at the end of each tube and limit tube life. The evaporation of the Tugnsten filament invades the mercury vapor limiting luminosity and tube life. Early ballasted fluorescent lighting systems are shown in FIGS. 1A and 1B. In FIG. 1A the ballast unit L is in series with filaments F and switch S, and in FIG. 1B, glow switch GS which opens after the filaments are heated to initiate a discharge.

Ballast transformers are often the most expensive part of commercial fluorescent lighting systems. There have been numerous past efforts to provide fluorescent lighting systems which do not use ballast transformers.

Electronic ballasts of the type shown in FIG. 1C are common in the art and are disclosed in International Rectifier Publication Application Notes AN-995, "Electronic Ballasts Using the Cost-Saving IR2155 Driver". In this circuit, two power switches Q1, Q2 are connected in a totem pole topology with the tube circuits consisting of an LC series resonant circuit with the lamp across one of the reactances. The switches are power MOSFETS driven to conduct alternately by windings on current transformer T. In this circuit, the primary winding is driven by current to the lamp circuit and operates at the resonant frequency of L and C. A starting pulse is provided by a starting circuit comprised of resistor R1 and capacitor C1 and DIAC D1 connected to one of the gates of one of the power switches. After oscillation is initiated, a high frequency square wave (30–80 kHz) excites the LC resonant circuit. The sinusoidal voltage across the reactance C is magnified by the Q at resonance and develops sufficient amplitude to strike the fluorescent lamp. In this system, the filaments of the lamp are connected in series with the series resonant circuit.

In the case of neon tubes as used in neon signage, conventional art uses high voltage (as a rule of thumb approximately 1000 volts per foot of sign) ballasted driver circuits which are inefficient, noisy, large, emit heat, require heavy high voltage insulation, are not usually dimmable).

THE PRESENT INVENTION

The basic objective of the present invention is to provide improved gas discharge light-producing systems and methods.

Another object of the present invention is to provide a more energy-efficient gas discharge light-producing system and method.

Another object of the invention is to provide a more energy-efficient light-producing system which is low in cost and operates at low voltages and low currents.

Another object of the invention is to provide a low-voltage (from about 2 to about 85–90 volts) light-producing system having a square wave voltage in the frequency range of about 75 kHz to about 3.5–4 MHz.

Another objective of this invention is to provide a light-producing system wherein one or more conventional gas discharge tubes is non-thermionically operated and driven by a low-voltage, high-frequency square wave source.

Another objective of this invention is to provide a gas discharge lighting system wherein multiple gas discharge tubes are electrically connected in series and non-thermionically driven by a low-voltage square wave voltage.

Another object of the invention is to provide a gas discharge light-producing system in which the light intensity is variable from low-level illumination to high-level illumination and from high-level illumination to low-level illumination.

According to the invention, non-thermionic, ballast-free, fluorescent lighting system comprises at least one gas discharge light-producing lamp or tube and a low-voltage (under 85–90 volts) square wave power supply. The square wave power supply incorporates a solid state switch means which is operated to generate a substantially square wave alternating current wave at the lamp or tube electrodes such that the voltage supplied to the electrodes reverses polarity more rapidly than the pattern of electron and ion density in the tube can shift so that electrons throughout the length of the device are continually accelerated and will, through several cycles of the applied square wave, create free electrons and ions throughout the tube's volume, in steady state operation and ionize the gas lighting lamp.

According to a preferred embodiment of the present invention, at least one light-producing device with electrodes (which may be conventional filaments or not) immersed in a gaseous discharge medium (such as noble gases, argon, neon, helium or xenon, and mercury vapor and mixtures thereof; however, other gases and gas mixtures can be used) and is non-thermionically (no heater or filament currents) driven with a low-voltage, high-frequency square wave voltage. In the preferred embodiment, the driver circuit includes an inverter circuit using two solid state switching devices which are connected in totem pole fashion across a direct current supply. The gate electrode of each switch transistor is connected in circuit with a primary winding for each switch device and a primary winding of the transformer. A starting circuit to start the oscillator is utilized to provide a positive turn-on pulse to the gate electrode of one of the transistor switches. When one of the transistor switches turns on, its voltage is rapidly switched to ground which starts the circuit in oscillation. In the preferred embodiment, the oscillating frequency is set at about 100 kHz, but the range of successful operation runs from about 75 kHz through about 4 MHz. Since there are no high voltages in the driver circuit, safe operation is assured.

Illumination or luminosity levels or dimming can be achieved by varying the voltage (or energy level) from the direct current supply. In the preferred embodiment, care is taken to assure that there are no spike voltages due to inductive kick and the like. Since the gas discharge lamps or devices are non-thermionically driven, the luminous efficiency is significantly improved. Moreover, at the preferred high frequency of 100 kHz, power supply components can be smaller.

A salient difference between the system of the present invention and traditional fluorescent lamp systems is the marked reduction of heat that accompanies a given light output, which is in turn the reason why their efficiency of conversion of electricity to light is so high. Some of the heat reduction is, of course, recognizable as resulting from the absence of direct heating of the filaments in each end of the tube by applied voltages. Some is also explained in terms of energy transfer in the high-field region which occurs near the momentary cathode. However, fluorescent and neon tubes in the system of the present invention are much cooler throughout their length, including areas that are at great distances from the filaments whose heating could not possibly be explained by conduction, radiation, or diffusive heat transfer through the low-pressure gas filling the tube. (The overall applied voltage is not large enough to suggest that local regions of high field exit in tubes driven by the present invention.)

Cooling along the length of the tube is believed to be explainable in terms of energy transferred to electrons and ions by the applied electric field. In the present invention, the square wave voltage applied to the tube reverses so frequently that positive ions in the discharge can build up little kinetic energy during a half-cycle of the applied voltage. In conventional systems, larger amounts of energy can be acquired by ions in one-half cycle. This kinetic energy contributes nothing to light output, but in conventional systems is rapidly transferred to the neutral gas molecules and thence to the walls of the tube.

A major source of energy loss in conventional fluorescent tubes is caused by need to almost completely reconstitute ionization in the tube, at the beginning of each half-cycle. This requires not only energy to ionize electrically neutral gas molecules, but additional energy representing losses when electrons collide with neutral gas molecules and thereby increase their motional energy without ionizing the molecules. The non-thermionic, ballast-free, low-voltage system of this invention also works on other gases different from mercury vapor, like neon, neon/helium, sodium vapor, neon/argon and others as well as plasma displays.

The fact that the system is non-thermionic and ballast-free eliminates the danger and cause of electrical fires caused by overheated ballast driven systems. The low-voltage eliminates the danger of electrical shock to humans, and because it is low voltage is essentially non-lethal to humans and thus safer.

The invention has the following further features:

(1) Being non-thermionic, you can intermingle gas discharge devices of different ratings, like the new "watt miser" 32 watt or the new 25 watts "energy savers" with the "standard" 40 watts (four footers). The light output essentially remains the same regardless of the tube rating. Today's usual shop lights can only use 40 watt regular tubes due to the shortcomings of the ballast as well as the use of chains to hang them because they can be a fire hazard. In order to demonstrate the efficacy of the system, a four-foot fluorescent tube (Sylvania rapid start F40) with blackened end (indicative of a non-working filament) was connected in series with a two-foot length of conventional neon signage tubing and both were successfully driven according to the principles of the present invention. Single Pin (slimline) Reduced Mercury content (Alto) fluorescent tubes also included.

(2) Being ballast-free, the fixture weight and operating temperature are substantially reduced, eliminating the need for chain hanging. The system is not a temperature driven fire hazard.

(3) Since the system is ballast-free, there is no need for a sound rating because the system is silent. The greatly reduced heat and weight will allow the use of a plastic housing, eliminating the "electric shock hazard" as well as the need for grounding, nescesary for the ballast to perform tubes in general should not be more than 1" from a grounded surface.

(4) Being of reduced heat, the system can be mounted in any orientation and in contact with standard combustible surfaces (wood, wallpaper, etc.).

(5) The tubes, if filamented, will keep emitting normal light even in the event that one or both filaments are inoperative or open-circuited.

(6) Most fluorescent arrays or multiple tube units consist of identical tubes in parallel. The plural or multiple tube array systems can comprise identical or different rated tubes in series.

(7) Standard 1¼ and 1½ inch diameter four-feet long fluorescent tubes filled with conventional mercury vapor or reduced mercury fluorescent tubes as well as T5 1" diameter (slim line) single pin fluorescent tubes and/or argon gases and simple non-filamentary electrodes, and even conventional tubes with non-working or burned out filaments have been successfully used in the practice of this invention. One of the features of the invention is the use of conventional fluorescent tubes with non-working filaments, or blackened ends can be rehabilitated using the invention disclosed herein.

(8) Flexible plastic tubing, or rigid plastic tubes, on flexible tubing the fluorescent mixture is prefered to be mixed with the tubing material such as used in surgical gas transport systems, with or without UV responsive phosphors incorporated on the walls therein, Lexan™ type hard plastic, shatter-proof gas retention vessels with simple discharge electrodes in the gas, with or without fluorescent coatings on the walls or fluorescent materials incorporated in the plastic, can be driven in accordance with the invention. In such cases, the darkening of the plastic due to UV bombardment with time can be advantageous, or the darkening can be prevented with a UV transparent blocking coating.

(9) Flexible plastic tubing and non-glass, plastic shatter-proof neon signage with electrodes at the ends and filled with one of the discharge gases noted above (as in conventional neon signs, for example) have been successfully driven using the driver circuit principles and methods disclosed herein.

DESCRIPTION OF THE DRAWINGS

The above and other objects, advantages and features of the invention will become more apparent when considered with the following specification and accompanying drawings wherein:

FIG. 2A is a general block diagram of the fluorescent lighting system incorporating the invention and FIG. 2B illustrates the various shapes of gas discharge devices to which the invention is applicable.

DETAILED DESCRIPTION OF THE INVENTION

Figure 1A:
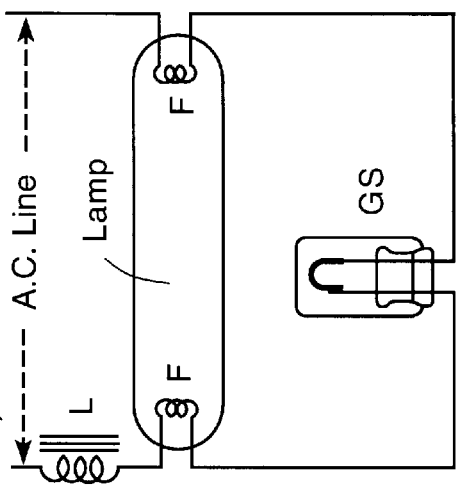
FIG. 1A is a circuit diagram of prior art transformer ballasted fluorescent lighting systems.
Figure 1B:
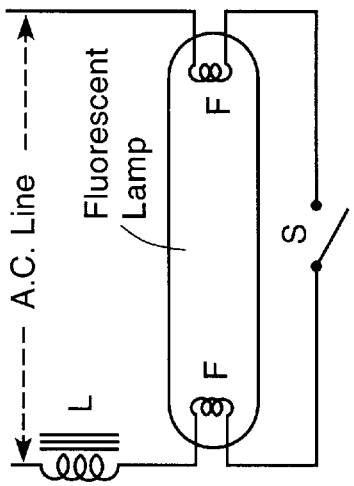
FIG. 1B is prior art ballasted fluorescent lighting systems with a glow switch starter.
Figure 1C:
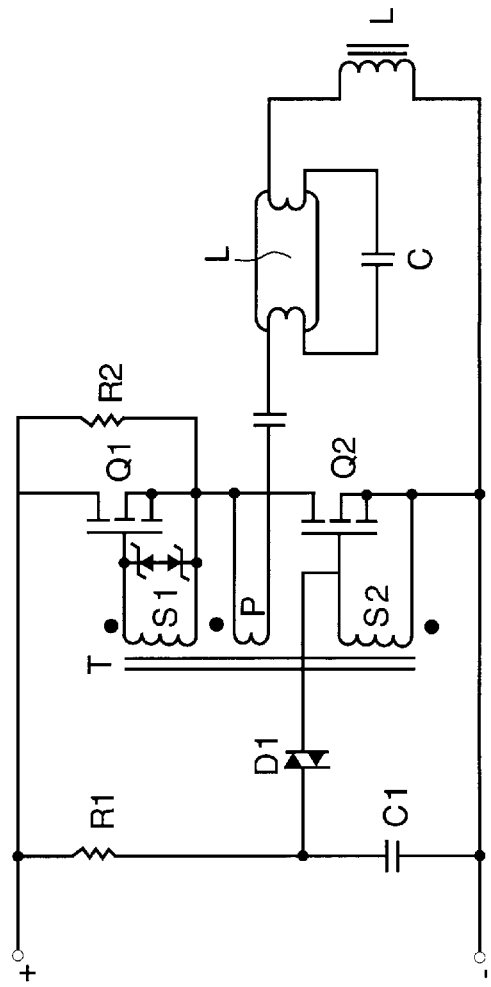
FIG. 1C is a circuit diagram of an electronic ballasted fluorescent lighting system.

The present invention is based on the discovery that using a rapidly repetitive low-voltage square wave alternating voltage, ionization will take place in gas discharge tubes at lower voltages and power. Since the half-cycle period of the square wave alternating voltage power according to the invention is very short (of the order of 5 microseconds for 100 kHz), there is very little opportunity for decay of the plasma between half-cycles. At start-up, ambient free electrons in the gas increase in energy in a half-cycle more than they lose energy due to collision processes. According to the invention, during one half-cycle, an electron will move in a roughly constant electric field. During each interval between collisions with neutral atoms, or ions, its kinetic energy will increase if its previous collision left it traveling with a component of velocity in the direction of the acceleration produced by the electric field. It will decrease if its previous collision left it moving without a component of velocity opposed to the field's acceleration. According to the invention, the square wave alternating supply voltage serves principally to raise the effective electron energy (or temperature). The current flowing consists of electrons flowing to the instantaneous anode and positive ions flowing to the instantaneous cathode where they recombine with electrons and are released as neutral atoms. Total gas pressure in the tube is sufficient to make the mean free path considerably less than the tube diameter and much less than its length. Most electrons and ions separate and recombine, in a small fraction of the overall length of the tube, rather than flowing as continuous streams along its axis.

The biggest problem in 60-Hz lamps is that ion and electron densities essentially virtually go to zero at the end of each half-cycle. To achieve light output again after a few milliseconds requires an active supply of electrons (from the filament) with high heating power for that filament. But, then, if the lamp system of the present invention starts at voltage levels far below that usually associated with plasma "breakdown", why does an equally low voltage applied constantly across a single tube not result in the same glowing plasma?

This can be explained in terms of the natural tendency of particles of a plasma subject to a static external field to move so as to create a space charge pattern and field that counteracts the applied field. The result of applying a voltage between two electrodes is to induce positive charge on the positive electrode and negative charge on the negative electrode, the absolute amount of charge depending on course on the capacitance between the two.

If free electrons and ions fill the space between these electrodes, the electrons are pulled toward the anode, and the positive ions toward the cathode, until in the space between there is no longer a field and therefore no means to cause further movement of the particles; a voltage drop, that is, region of high field, will exist very close to each of the two electrodes. The electrons (and ions) in the main part of the tube will not be further affected by the field; when electrons reach the high field region near the anode, they will probably be accelerated to half the applied voltage within less than one mean free path of the anode's surface and hence will be unlikely to produce ionization.

In the gas discharge light-producing system of this invention, the applied square wave voltage is alternated rapidly enough that the charged particles cannot move enough to accumulate near cathode and anode during a half-cycle of the applied voltage. Thus, the field remains almost continuously active in accelerating electrons within the main body of the tube.

Figure 2A:
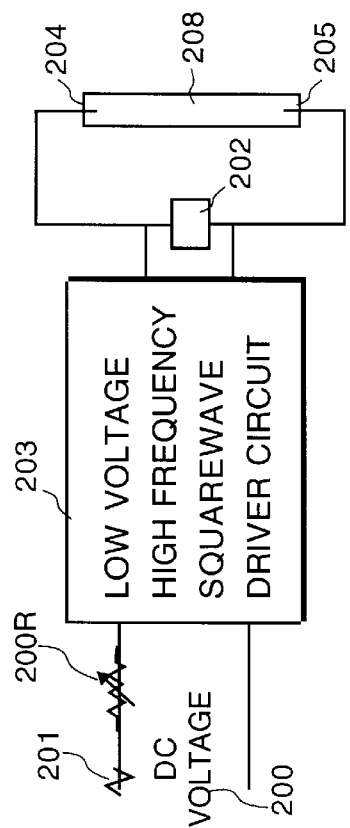

FIG. 2A is a schematic block diagram of a fluorescent lighting system incorporating the invention. A direct current (DC) power supply 200 is protected by a fast-acting fuse 201 and/or a crowbar circuit 202 which provides fast-acting protection of the circuit in the event of a fault. The DC voltage is applied to square wave inverter circuit 203 which converts the DC voltage to a low-voltage (between about 3 to about 20 volts RMS), AC square wave voltage having a high-frequency (between about 75 kHz and about 4 MHz) which is applied to electrodes 204 and 205 of a gas discharge device 208 which, in this embodiment, is a fluorescent tube. The current is very low so in comparison with light output equivalent to a conventional 60 Hz, thermionically operated fluorescent tube or lamp, the luminous efficiency is significantly improved. Moreover, the fluorescent lamp or tube can be straight, folded or looped as indicated in FIG. 2B. A rheostat 200R can be used to adjust or vary the voltage or energy level from the source 203 to gas discharge device 208 and thereby dim or vary the level of luminosity from the lamp. Since the system does not depend on a large ignition voltage level, the luminosity can be varied from low to high and back to low. In contrast, most conventional dimming circuits for fluorescent lamps require starting with a relatively high luminosity or level of illumination and then reducing the level to a desired point. If the gas discharge device is a neon sign tube, for example, various advertising or decorative and aesthetic lighting effects can be achieved by a computer controlled programmed of the varying the voltage by varying resistance 200 R and/or the voltage at source 200.

Figure 3:
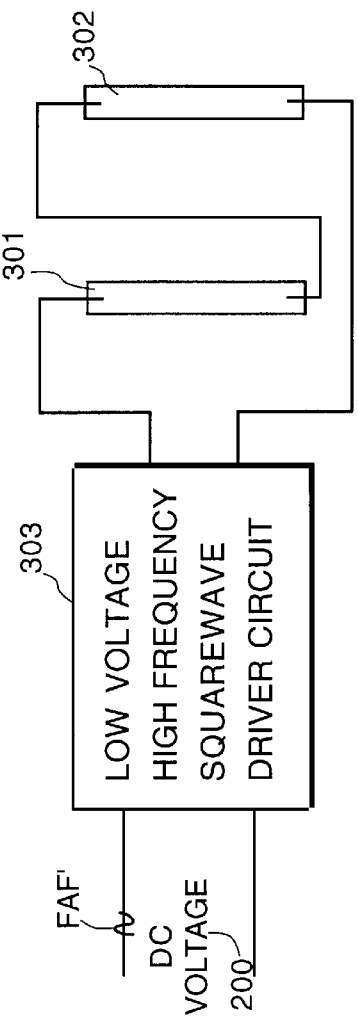
FIG. 3 is a general block diagram of a gas discharge driving system incorporating a preferred embodiment of the invention.

FIG. 3 is a schematic block diagram illustrating two gas discharge devices 301 and 302 driven by low-voltage, high-frequency square wave inverter circuit 303. Note that the tubes 301 and 302 are connected in series so that while the square wave inverter circuit 303 can be of the same capacity as the square wave inverter circuit 202, if tubes 301 and 302 have the same length and diameter as gas discharge device 206, the volume of gas is essentially doubled. Note that the devices 301 and 302 are non-thermionically driven, even though the tubes may incorporate conventional filaments (not shown).

Figure 4:
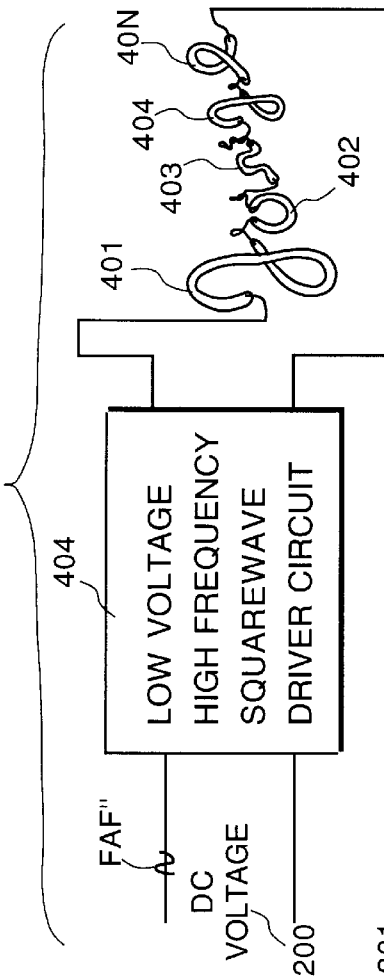
FIG. 4 is a general block diagram of a lighting system showing the same driver system driving a neon tube or sign tube.

FIG. 4 is a schematic block diagram illustrating another variety of gas discharge devices, neon sign portions 401, 402 . . . 40N constituting a sign driven by a low-voltage, high-frequency, square wave inverter circuit 404 While shown as series connected, they could be connected in parallel, or combination of serial and parallel. In this case, the discharge devices 401, 402 . . . 40N are serially connected, the middle tubes 402 . . . are not directly connected to the output terminals of the inverter circuit 404. The total volume of gas driven is the sum of the volumes of neon gas in the individual of gas discharge devices, none of which is thermionically energized or excited. If all of the discharge devices volumetrically equal gas-wise, and are identical or essentially the same they all illuminate with equal intensity. As noted earlier, the tubes can be coated with UV responsive phosphor or have UV responsive phosphors incorporated in the plastic or glass tubes. In such case, a gaseous medium which is rich in UV on discharge is used (such as mercury vapor and argon). Also, the gaseous medium can be varied to vary the color of light produced. The tubes 401, 402 . . . 40N can be flexible plastic or shatterproof plastic thereby avoiding the well known problem of breakage or fragility of conventional neon signage. Since the tubes 401, 402 . . . 40N can be easily wired in series, the letters or symbols can be prefabricated or premanufactured and wired in series thereby reducing costs and production times.

Figure 5:
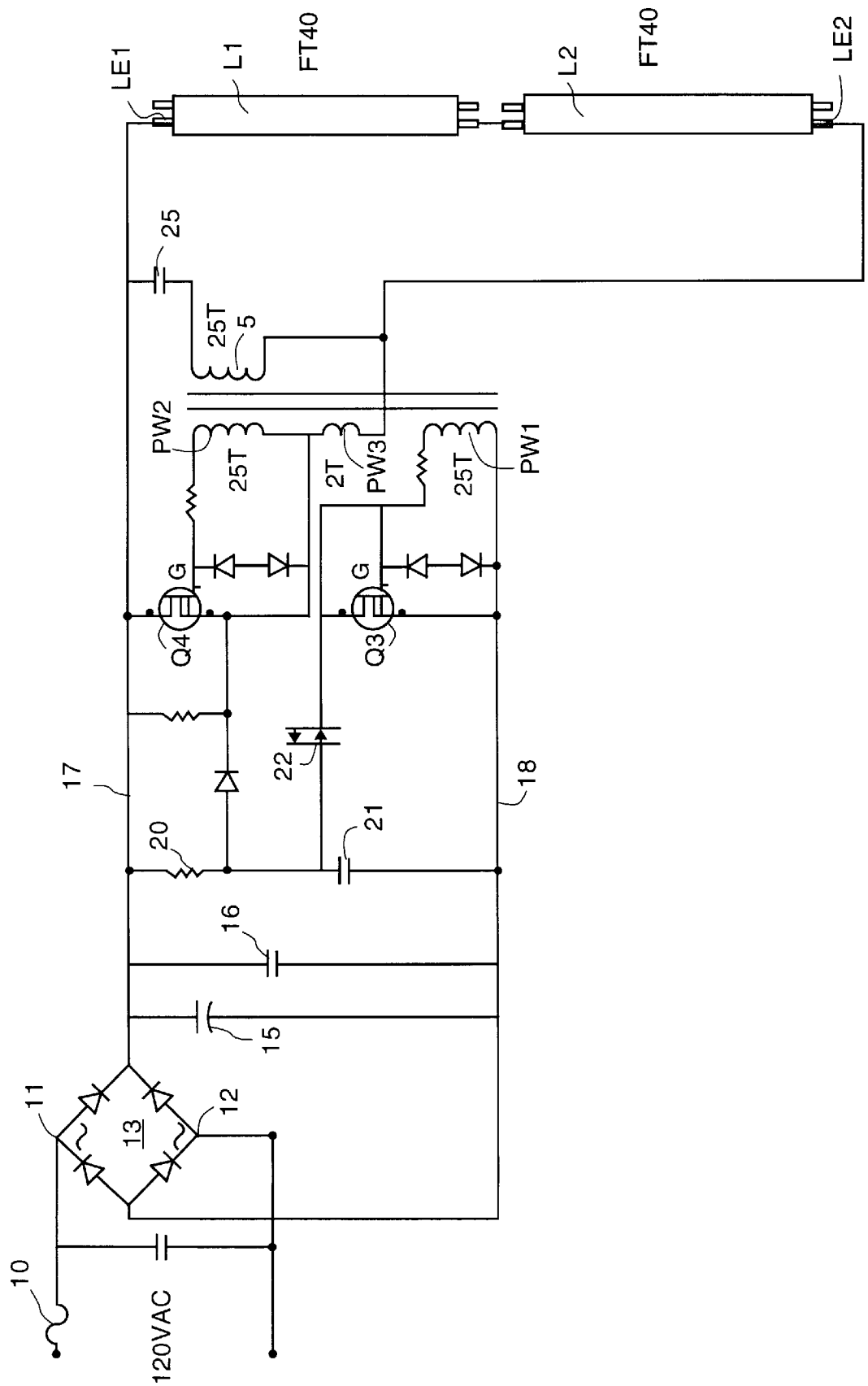
FIG. 5 is a detailed circuit diagram of a preferred embodiment of the invention.

A preferred embodiment of the invention for driving two FT40 fluorescent tubes in series is illustrated in FIG. 5. The component values and component types are merely exemplary. This produces a square wave voltage at about 100 kHz with sharp transitions such that the voltage supplied to the lamp L1 electrode LE1 and lamp L2 electrode LE2 reverses polarity more rapidly than the pattern of electron and ion density in the gaseous volume can shift so that electrons throughout the length of the tube are continually oscillated and will, through several cycles of the square wave, create ions throughout the tubes, gaseous volume, in steady state operation.

In this embodiment of the invention, alternating current (120 VAC for example) is applied through a fast-acting fuse 10 to terminals 11 and 12 of full wave bridge rectifier 13 which provides DC voltage which is filtered by an electrolytic capacitor 15. In this embodiment fast-acting fuse 10 or a crowbar circuit at the output is required to prevent damage to the circuit if the lamp(s) is removed from the circuit. High-frequency filter capacitor 16 is connected across the AC input to the bridge rectifier 13. Other sources of direct current voltage, such as batteries, solar cells, etc., may be used to provide operating energy.

The fluorescent lamp driver comprises an oscillator circuit using two solid state switching devices or transistors Q3 and Q4 (HEXFET'S, IRF624). The switching transistors Q3 and Q4 are connected in totem-pole-fashion across the direct current supply lines 17 (+) and 18 (− or ground). The gate electrode G circuit of each switch driver Q3 and Q4 is connected in circuit with a primary winding PW1 (twenty-five turns) for switch device Q3 and primary winding PW2 (twenty-five turns) for switch device Q4.

Resistor 20 and capacitor 21, with DIAC 22 form a starting circuit for the lower transistor switch Q3. In this embodiment, when the DIAC 22 reaches about 35 volts, a positive turn on pulse is applied to gate G1 of the lower switch device Q3. When switch Q3 switches on, the drain voltage is rapidly switched to ground which starts circuit oscillation. Current flowing through the two turn primary winding PW3 provides gate drive voltages for switching the switch devices Q3 and Q4. This causes the circuit to oscillate at about 100 kHz. Primary winding PW3 speeds up switching of the switches Q3 and Q4 by an order of magnitude. This is caused by a feedback switching action speeding up the switching operation of switches Q3 and Q4.

Figure 6:
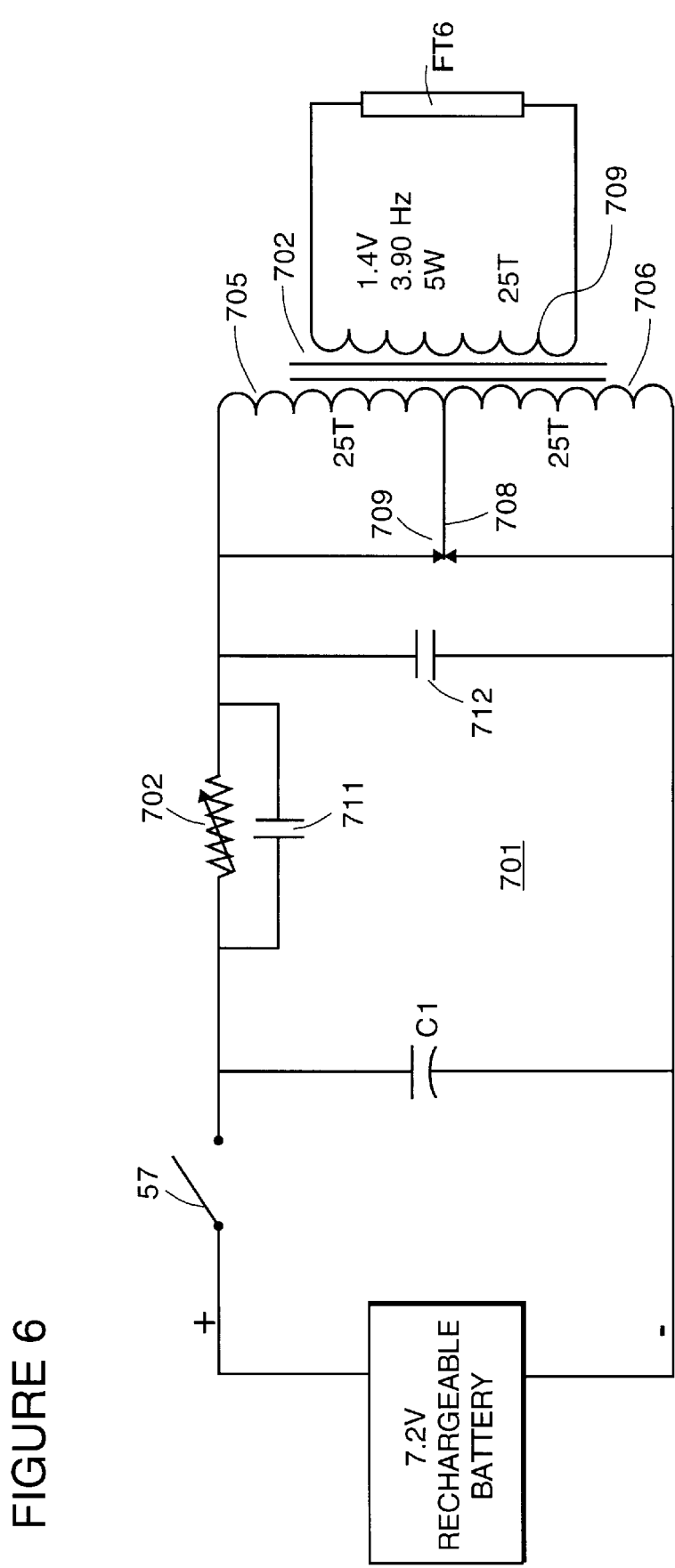
FIG. 6 is a circuit diagram illustrating a further preferred embodiment of the invention.

FIG. 6 illustrates a low-voltage square wave inverter circuit requiring a minimum of five components (the electrolytic filter capacitor C1 is deemed to be a part of the DC power source or supply). Switch 57 couples DC voltage (7.2 volts for example) from a battery to the low-voltage square wave inverter drive circuit 701 via dimmer resistor 702 and filter capacitor 701. This driver circuit includes an oscillation transformer 702 having a center tapped primary winding 704 having primary winding 705 and 706 with the center tap 707 connected to gate electrode 708 of oscillating diode transistor 709. The opposing ends of oscillating diode D1 are connected to the upper and lower ends of the primary windings 705 and 706. As shown, in transformer 702, primary windings 705 and 706 and second winding 709 have about 25 turns each. A capacitor shunts the oscillating transistor/diode 709. The exemplary circuit components are as follow:

| | |
|---|---|
| Fluorescent tube | FT6 |
| Resistor R1 | 1500 Ohms |
| Capacitor C1 | 47UF 10 V Electrolytic |
| Transistor diode 709 | 5609/6BC/ECB |
| Capacitor 711 | 2A562K |
| Capacitor 712 | 2A22K |

The output to the fluorescent tube is about 1.4 volts RMS at 3.9 MHz open circuit and 1.7 MHz, square wave at the tube. Thus, the system has no ballast transformer, no thermionic heating of filaments, no starter circuit, and produces light in a more energy-efficient way.

Figure 7:
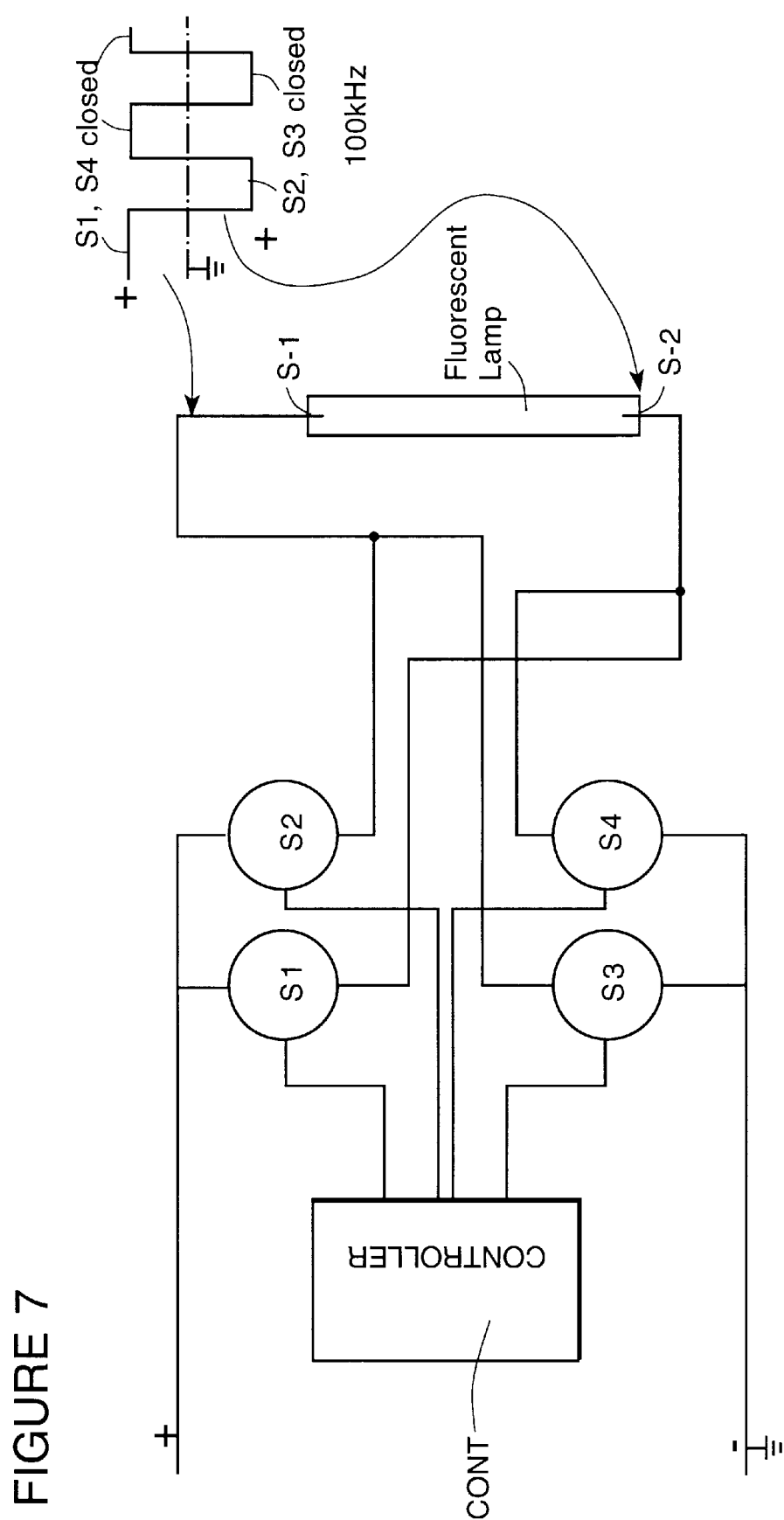
FIG. 7 is a diagrammatic illustration of a further embodiment of the invention.

FIG. 7 diagrammatically illustrates a transformer-less square wave inverter circuit. Here, the positive (+) and negative (−) terminals of a direct current source are alternately connected to opposing electrodes of the fluorescent lamp(s). In this case, when switches S3 and S4 are closed simultaneously or at the same time (preferably by the same signal from controller CONT, the positive terminal (+) is connected to electrode 8-1 and the negative terminal (−) is connected directly to electrode 8-2. When the switches S1 and S2 are simultaneously closed (and switches S3 and S4 are open) by controller CONT, the positive terminal (+) is connected directly to lamp electrode 8-2 and the negative terminal (−) is connected to fluorescent lamp electrode 8-1. Controller CONT can operate the switches in the range of about 75 kHz to about 3.9 MHz and preferably operates the switches to cause the square wave applied to lamp electrodes 8-1 and 8-2 to be at a frequency of about 100 kHz.

In this invention, the magnitude of the alternating voltage at the electrodes is of small significance in initiating the discharge reaction, allowing the capability to start the production of visible light at a low or high intensity—since the light generated is in direct proportion to the total energy input. (There is no need for a large "starting strike" voltage to ionize the gas.)

Experiments with a transparent Phillips mercury vapor electric discharge lamp model H39KB-175 (175 watts)

connected to the 1.2 watt driver (shown in FIG. 6) shows the same behavior and characteristics of the fluorescent application. It is believed that the reaction starts at one end of the tube and rapidly extends to the other or far end and then gets stable. Experiments connecting only one electrode supports this theory. This is why several gas discharge devices in series can be used, because the field reversal is achieved before the original distal reaction in the tube collapses.

While preferred embodiments of the invention have been described and illustrated, it will be appreciated that other embodiments, adaptations and modifications of the invention will be readily apparent to those skilled in the art.

What is claimed is:

1. A low-voltage, non-thermionic, ballast-free gas discharge light-producing system comprising at least one gas discharge device with electrodes spaced in a gaseous discharge medium, a light transmissive envelope confining the gaseous discharge medium at a predetermined pressure between said electrodes, and a power supply, said power supply including a direct current source, a solid state switch means connected between said direct current source and said electrodes and resonant LC free means connecting said solid state switch means to said electrodes, said solid state switch means being operated to generate a substantially square wave alternating current voltage at said electrodes so that the voltage applied to the gaseous medium between said electrodes reverses polarity more rapidly than the pattern of electron and ion density in the tube can shift and electrons throughout the length of the envelope are continually accelerated and will, through several cycles of said square wave voltage create ions throughout the envelope's volume, in steady state operation.

2. A low-voltage, non-thermionic, ballast-free lighting system comprising at least one light transmissive envelope with spaced electrodes and a gaseous discharge medium filling said light transmissive envelope, said light transmissive envelope confining said gaseous discharge medium at a predetermined pressure between said electrodes, and a power supply, said power supply having a transformer with primary and secondary windings, a direct current source, a switch means connected between said primary winding and said source of direct current and electrical conductors connecting said secondary winding to said electrodes, said switch means and said transformer primary winding being operated to generate and apply a substantially square wave alternating current wave voltage at said electrodes so that the voltage applied to the gaseous discharge medium between said electrodes reverses polarity more rapidly than the pattern of electron and ion density in the light transmissive envelope can shift and electrons throughout the length of the light transmissive envelope are continually accelerated and will create ions throughout the envelope's volume, in steady state operation.

3. A low-voltage, non-thermionic gaseous discharge lighting system comprising at least one gaseous discharge device, each said at least one discharge device having spaced electrodes in a light transmissive envelope confining a gaseous discharge medium at a predetermined pressure between said electrodes, and a direct current power supply, a solid state switch means connected between said electrodes and said direct current power supply and said electrodes, said switch means being operated to generate a substantially square wave alternating current voltage at said electrodes so that the voltage supplied to said electrodes reverses polarity more rapidly than the pattern of electron and ion density in the gas can shift and electrons throughout the length of each of the discharge devices are continually accelerated and will, through several cycles of said square wave voltage create ions throughout the gaseous discharge medium between said electrodes, in steady state operation.

4. A gas discharge lighting system comprising in combination a gas discharge lamp means, a source of a low-voltage, high-frequency alternating current substantially square wave voltage having a pair of output terminals and a resonant LC free circuit connecting said low-voltage, high-frequency square wave voltage to said gas discharge lamp means to non-thermionically excite and illuminate said gas discharge lamp means.

5. The gas discharge lighting system defined in claim 4 wherein said low-voltage, high-frequency square wave voltage is in the frequency range of about 75 kHz to about 3.5 MHz.

6. The gas discharge lighting system defined in claim 4 wherein said low-voltage, high-frequency square wave voltage has a frequency of about 100 kHz.

7. The gas discharge lighting system defined in claim 4 wherein said low voltage is in the range of about 2 volts to about 90 volts.

8. The gas discharge lighting system defined in claim 4 wherein said low voltage is in the range of about 2 to about 90 volts and has a frequency in the range of about 75 kHz to about 3.5 MHz.

9. The gas discharge lighting system defined in claim 4 wherein said voltage is about 2 volts and said frequency is about 3.5 MHz.

10. The gas discharge lighting system defined in claim 4 wherein said gas discharge lamp means includes at least two conventional discharge tubes selected from 1½", 1¼"and 1" diameter tubes and means connecting the selected said at least two tubes in series across said pair of output terminals.

11. The gas discharge lighting system defined in claim 4 wherein said gas discharge lamp means includes at least three gas discharge devices and means connecting said at least three gas discharge devices in electrical series across said pair of output terminals.

12. The gas discharge lighting system defined in claim 4 including means to protect said source of low-voltage, high-frequency, square wave voltage from an open circuit at said pair of output terminals.

13. The gas discharge lighting system defined in claim 12 wherein said means to protect includes a fast-acting fuse.

14. The gas discharge lighting system defined in claim 12 wherein said means to protect includes a crowbar circuit connected across said output terminals.

15. The gas discharge lighting system defined in claim 10 wherein said low voltage is from about 2 volts to about 90 volts and the frequency is from about 75 kHz to about 3.5 MHz.

16. The gas discharge lighting system defined in claim 11 wherein said low voltage is from about 2 volts to about 90 volts and the frequency is from about 75 kHz to about 3.5 MHz.

17. The gas discharge lighting system defined in claim 10 wherein said low voltage is about 16–18 volts and said frequency is about 100 kHz.

18. The gas discharge lighting system defined in claim 4 wherein said source includes one or more switching transistors and an oscillation transformer.

19. The gas discharge lighting system defined in claim 18 wherein said voltage is in the range of 2–90 volts and said frequency is in the range of about 75 kHz to about 3.9 kHz.

20. A lighting system comprising two or more gas discharge lamp devices, a low-voltage, high-frequency, substantially square wave voltage source having a pair of output terminals and a resonant LC free circuit connecting said two or more gas discharge lamp devices in series across said pair of output terminals to non-thermionically excite and illuminate said pair of gas discharge lamp devices.

21. The gas discharge lighting system defined in claim 20 wherein said low-voltage, high-frequency, square wave voltage source operates in the range of about 75 kHz to about 3.5 MHz.

22. The gas discharge lighting system defined in claim 20 wherein said low-voltage, high-frequency, square wave voltage source operates at about 100 kHz.

23. The gas discharge lighting system defined in claim 4 wherein said discharge lamps are neon filled tubes having electrodes and said electrodes being connected in series across said pair of output terminals.

24. The gas discharge lighting system defined in claim 23 wherein said neon filled tubes are plastic.

25. The gas discharge lighting system defined in claim 23 wherein said neon filled plastic tubes are made of flexible plastic.

26. The gas discharge lighting system defined in claim 20 wherein said voltage is in the range of about 2 volts to about 90 volts.

27. The gas discharge lighting system defined in claim 20 wherein said voltage is about 2 volts RMS.

28. The gas discharge lighting system defined in claim 20 wherein said voltage is about 2–4 volts RMS and said frequency is about 3.5 MHz.

29. The gas discharge lighting system defined in claim 20 wherein the frequency of said square wave voltage is about 100 kHz.

30. The gas discharge lighting system defined in claim 29 including means to protect said voltage source of a low-voltage, high-frequency, square wave voltage from an open circuit at said pair of output terminals.

31. The fluorescent lighting system defined in claim 30 wherein said means to protect includes a fast-acting fuse.

32. The fluorescent lighting system defined in claim 30 wherein said means to protect includes a crowbar circuit connected across said output terminals.

33. The fluorescent lighting system defined in claim 20 including means to vary the energy level delivered from said voltage source to said lamp devices to vary the level of luminosity emitted by said lamp devices.

34. A method of igniting a gas discharge device having spaced electrodes immersed in a gas at voltages far below the required starter ignition voltage for cold cathodes comprising:
providing a low-voltage square wave alternating voltage source of between about 2–85 volts and between about 75 kHz and 4 MHz,
and applying a low-voltage square wave alternating current from said source directly to said gas discharge device so that the voltage on said lamp electrodes reverses its polarity more rapidly than the pattern of electron and ion density in the gas can shift.

35. The method defined in claim 34 wherein said voltage is in the range of about 2 volts RMS to about 85 volts RMS.

36. The method defined in claim 34 wherein said frequency is about 3.5 MHz and said voltage is about 2 volts.

37. The method defined in claim 34 wherein said frequency is about 100 kHz and said voltage is about 16 volts.

38. The method defined in claim 34 including the step of varying the energy level from said source to said lamp to vary the level of luminosity emitted by said gas discharge device.

39. An electric light source comprising one or more gas filled tubes, said one or more gas filled tubes being in the shape of a sign or a portion thereof, electrodes at the ends of said each of said one or more gas filled tubes and a source of low voltage, high frequency square wave alternating voltage connected to said electrodes.

40. The electric source defined in claim 39 wherein said one or more gas filled tubes are shatterproof plastic.

41. The electric light source defined in claim 39 wherein said one or more gas filled tubes are flexible plastic tubes.

42. An electric light source comprising in combination:
a source of low-voltage, high-frequency, square wave alternating voltage in the frequency range of about 75 kHz to about 4 MHz,
a filamented fluorescent tube in which one or more filaments have opened, and
circuit means connecting said filamented fluorescent tube to said source.

43. A non-thermionic driver system for driving a pair of gas discharge tubes selected from 1½", 1¼" and 1" diameter gas discharge tubes, each gas discharge tube having first and second electrodes, respectively, means conductively connecting said first electrodes together so that said pair of gas discharge tubes are connected in electrical series, and a low voltage, high-frequency substantially square wave alternating current voltage source having a pair of output terminals connected to said second electrodes, respectively.

44. The non-thermionic driver system defined in claim 43 wherein said low voltage is between about 2 and about 90 volts and at a frequency between about 75 kHz and about 4 MHz.

45. A driver system for two gas discharge tubes comprising a low voltage substantially square wave, alternating current voltage source having a pair of output terminals and means connecting said two gas discharge lamps in series across said pair of output terminals so that the voltage applied to the selected tubes reverses more rapidly than the pattern of electron and ion density in the gas discharge tubes can shift and electrons are accelerated and through several cycles of the square wave voltage create ions throughout said tubes in steady state operation.

46. A method of non-thermionically driving two or more gas discharge tubes comprising:
providing a low voltage, substantially square wave, alternating current voltage source having a frequency greater than 75 kHz, and
connecting said two or more gas discharge tubes in series and directly across said low voltage, square wave alternating current voltage source.

47. The method defined in claim 46 wherein said square wave alternating current voltage is under about 90 volts and greater than about 2 volts.

48. The method defined in claim 47 wherein said frequency is about 100 kHz.

49. A non-thermionic, voltage driver system for a gas discharge lighting lamp comprising a substantially square wave, alternating current voltage generator having a frequency greater than about 75 kHz and a pair of output terminals and resonant LC free circuit means connecting said gas discharge lamp across aid output terminals.

* * * * *